(12) United States Patent
Hies et al.

(10) Patent No.: US 9,726,590 B2
(45) Date of Patent: Aug. 8, 2017

(54) SUSPENDED SEDIMENT METER

(71) Applicant: HydroVision Asia Pte Ltd, Singapore (SG)

(72) Inventors: Thomas Hies, Singapore (SG); Juergen Skripalle, Irsee (DE); Nguyen Hoang Ha, Singapore (SG)

(73) Assignee: HYDROVISION ASIA PTE LTD, Singapore (SG)

( * ) Notice: Subject to any disclaimer, the term of this patent is extended or adjusted under 35 U.S.C. 154(b) by 136 days.

(21) Appl. No.: 14/407,468

(22) PCT Filed: Jul. 1, 2013

(86) PCT No.: PCT/IB2013/055380
§ 371 (c)(1),
(2) Date: Dec. 12, 2014

(87) PCT Pub. No.: WO2014/002078
PCT Pub. Date: Jan. 3, 2014

(65) Prior Publication Data
US 2015/0153262 A1 Jun. 4, 2015

(30) Foreign Application Priority Data
Jun. 29, 2012 (SG) .................................. 201204870

(51) Int. Cl.
G01N 29/032 (2006.01)
G01N 15/04 (2006.01)
(Continued)

(52) U.S. Cl.
CPC ............. G01N 15/04 (2013.01); G01N 29/02 (2013.01); G01N 29/032 (2013.01);
(Continued)

(58) Field of Classification Search
CPC ........................................... G01N 2291/02416
(Continued)

(56) References Cited

U.S. PATENT DOCUMENTS 4,052,793 A * 10/1977 Coughlin ................. G05D 3/00
324/537
4,249,422 A * 2/1981 Gaunaurd .............. G01N 29/12
73/589
(Continued)

FOREIGN PATENT DOCUMENTS

DE 3438798 A1 4/1986
EP 0989397 A1 3/2006
(Continued)

OTHER PUBLICATIONS

Examiner Chang, Bong Ho, International Search Report, Jun. 29, 2012, 3 pages.*
(Continued)

Primary Examiner — Clayton E Laballe
Assistant Examiner — Kevin Butler
(74) Attorney, Agent, or Firm — Hydrovision Asia Pte Ltd; George Liu

(57) ABSTRACT

The application provides a device for measuring at least one parameter value of a suspended sediment of a fluid. The device includes a backscattering transducer module, a storage unit, and a calculation unit. The backscattering transducer module comprises a source module and a receiver module. The source module transmits at least three acoustic signals with different fixed characterizing measurement frequencies while the receiver module measures at least three echo level values of echo signals, which correspond with the at least three acoustic signals. The storage unit stores a data set of pre-determined echo level values with a data set of pre-determined suspended sediment parameter values. The
(Continued)

Figure 1:
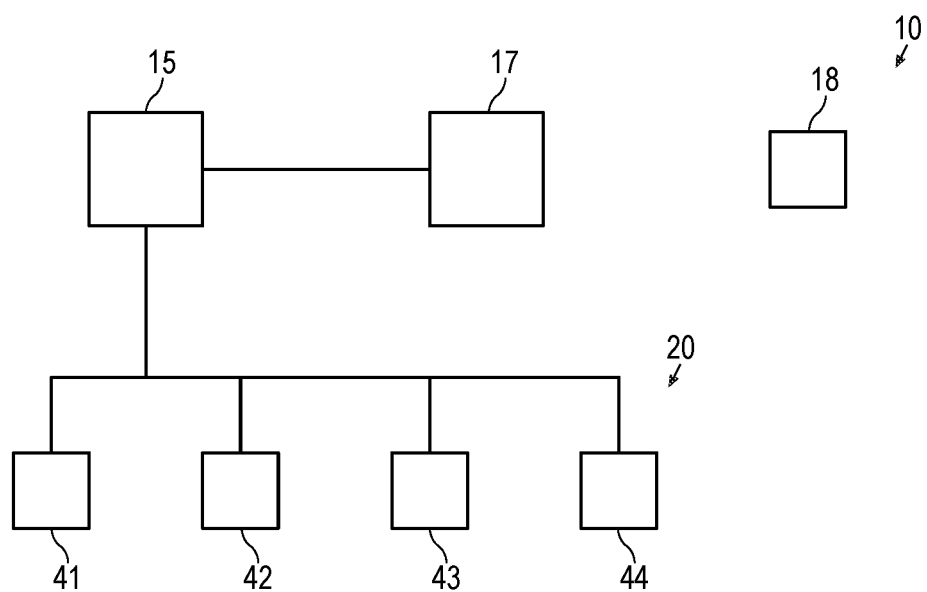

calculation unit derives at least one suspended sediment parameter value from the data sets and the at least three echo level values.

15 Claims, 15 Drawing Sheets

(51) Int. Cl.
    *G01N 29/02*     (2006.01)
    *G01N 29/34*     (2006.01)
    *G01N 29/44*     (2006.01)

(52) U.S. Cl.
    CPC ......... *G01N 29/348* (2013.01); *G01N 29/449* (2013.01); *G01N 29/4427* (2013.01); *G01N 2291/012* (2013.01); *G01N 2291/022* (2013.01); *G01N 2291/02408* (2013.01); *G01N 2291/02416* (2013.01); *G01N 2291/02836* (2013.01); *G01N 2291/044* (2013.01)

(58) Field of Classification Search
    USPC ...................................................... 73/61.75
    See application file for complete search history.

(56) References Cited

U.S. PATENT DOCUMENTS

| | | | | | |
|---|---|---|---|---|---|
| 4,266,185 | A | * | 5/1981 | Charlesworth | G01R 27/14 324/716 |
| 4,706,509 | A | * | 11/1987 | Riebel | G01N 15/02 73/24.03 |
| 4,718,269 | A | * | 1/1988 | Der Kinderen | G01F 1/663 73/19.03 |
| 4,947,683 | A | * | 8/1990 | Minear | E21B 47/101 73/152.32 |
| 5,125,264 | A | * | 6/1992 | Beuzard | G01S 15/18 73/61.75 |
| 5,483,499 | A | * | 1/1996 | Brumley | G01S 15/8959 367/89 |
| 5,485,432 | A | * | 1/1996 | Aechter | G01S 7/539 367/12 |
| 6,119,510 | A | * | 9/2000 | Carasso | G01N 15/0205 356/437 |
| 6,262,942 | B1 | * | 7/2001 | Stanton | G01F 23/296 367/90 |
| 6,487,916 | B1 | * | 12/2002 | Gomm | G01F 1/667 73/861.27 |
| 6,983,208 | B2 | * | 1/2006 | Metcalf | G01F 1/002 702/45 |
| 8,120,375 | B2 | * | 2/2012 | Foster | G01R 1/07314 324/756.03 |
| 8,134,381 | B2 | * | 3/2012 | Abe | G01R 31/2886 324/754.07 |
| 8,525,538 | B2 | * | 9/2013 | Kim | G01R 31/2887 324/754.11 |
| 9,110,131 | B2 | * | 8/2015 | Dietrich | G01R 31/2891 |
| 9,176,185 | B2 | * | 11/2015 | Canegallo | G01R 31/2889 |
| 9,347,970 | B2 | * | 5/2016 | Shinohara | G01R 1/0491 |
| 2002/0089343 | A1 | * | 7/2002 | Khoury | G01R 1/06711 324/755.05 |
| 2003/0122567 | A1 | * | 7/2003 | Miller | G01R 31/2875 324/750.08 |
| 2004/0113640 | A1 | * | 6/2004 | Cooper | G01R 3/00 324/750.25 |
| 2004/0139792 | A1 | * | 7/2004 | Cobb | G01N 29/032 73/61.75 |
| 2004/0145386 | A1 | * | 7/2004 | Byun | G01R 31/2886 324/754.19 |
| 2007/0282539 | A1 | | 12/2007 | Metcalf et al. | |
| 2008/0290882 | A1 | * | 11/2008 | Rogers | G01R 1/36 324/755.11 |
| 2009/0273357 | A1 | * | 11/2009 | Kamata | G01R 1/06727 324/754.03 |
| 2010/0026331 | A1 | * | 2/2010 | Chong | G01R 1/07342 324/754.03 |
| 2010/0039130 | A1 | * | 2/2010 | Kumagai | H01L 22/12 324/754.03 |
| 2011/0316576 | A1 | * | 12/2011 | Kataoka | G01R 31/2891 324/756.03 |
| 2012/0068728 | A1 | * | 3/2012 | Kataoka | G01R 31/3025 324/756.03 |
| 2012/0194213 | A1 | * | 8/2012 | Komatsu | G01R 31/2887 324/756.03 |
| 2012/0242363 | A1 | * | 9/2012 | Breinlinger | G01R 1/06716 324/756.02 |
| 2013/0063171 | A1 | * | 3/2013 | Kouno | G01R 31/2886 324/750.25 |
| 2014/0203834 | A1 | * | 7/2014 | Chang | G01R 1/07342 324/756.03 |
| 2015/0070038 | A1 | * | 3/2015 | Joo | G01R 1/07378 324/754.07 |
| 2015/0153262 | A1 | * | 6/2015 | Hies | G01F 1/74 73/61.75 |
| 2016/0069988 | A1 | * | 3/2016 | Foote | G01S 15/025 367/13 |

FOREIGN PATENT DOCUMENTS

| | | |
|---|---|---|
| JP | 2002139456 A | 5/2002 |
| WO | 9107646 A2 | 5/1991 |
| WO | 9528654 A1 | 10/1995 |

OTHER PUBLICATIONS

Austin J. C et al., "Ultrasonic wave propagation in colloid suspensions and emulstions: recent experimental results", Ultrasonics, GB, IPC Science and Technology Press Ltd. Guilford, vol. 34, No. 2 pp. 369-374 (1996).*

J.S. Tebbutt et al., "Ultrasonic wave propagation in colloid suspensions and emulstions: a comparison of four models", Ultrasonics, GB, IPC Science and Technology Press Ltd. Guilford, vol. 34, No. 2 pp. 363-368 (1996).*

Examiner Chang, Bong Ho, PCT/IB2013/055380, PCT Written Opinion of the International Searching Authority, Nov. 22, 2013, 6 pages.*

Examiner Chang, Bong Ho, International Search Report, PCT/IB2013/055380, Jun. 29, 2012, 3 pages.*

Smerdon, A. M. & Thorne, P. D., A Coastal Deployment of a Commercial Multiple Frequency Acoustic Backscatter Sediment Profiler, PECS 2008: Physics of Estuaries and Coastal Seas, Liverpool, UK, Aug. 25-29, 2008. Liverpool, 357-360.

* cited by examiner

FIXED TEMPERATURE T = 25 DEGREE CELSIUS, SALINITY S = 10 PSU,
DISTANCE R = 0.325 m, BIN SIZE = 0.03 m

| SSC [kg/m3] | MEDIAN [μm] | SLOPE | f1 [dB] 0.5 [MHz] | f2 [dB] 1.2 [MHz] | f3 [dB] 2.5 [MHz] | f4 [dB] 5.0 [MHz] |
|---|---|---|---|---|---|---|
| 0.05 - 0.06 | 53-55 | 0.0161 - 0.0162 | 133.7 - 134.6 | 144.1 - 145.0 | 143.4 - 144.2 | 133.2 - 134.0 |
| 0.06 - 0.07 | 53-55 | 0.0161 - 0.0162 | 134.5 - 135.3 | 144.9 - 145.6 | 144.1 - 144.9 | 134.0 - 134.7 |
| 0.07 - 0.08 | 53-55 | 0.0161 - 0.0162 | 135.1 - 135.8 | 145.5 - 146.2 | 144.8 - 145.5 | 134.6 - 135.2 |
| 0.08 - 0.09 | 53-55 | 0.0161 - 0.0162 | 135.7 - 136.4 | 146.1 - 146.7 | 145.4 - 146.0 | 135.2 - 135.7 |
| 0.09 - 0.1 | 53-55 | 0.0161 - 0.0162 | 136.2 - 136.8 | 146.6 - 147.2 | 145.9 - 146.4 | 135.7 - 136.1 |
| ⋮ | | | | | | |
| 1.0 - 1.1 | 53-55 | 0.0161 - 0.0162 | 146.7 - 147.2 | 156.9 - 157.4 | 155.6 - 156.0 | 143.9 - 144.1 |
| 1.1 - 1.2 | 53-55 | 0.0161 - 0.0162 | 147.1 - 147.6 | 157.3 - 157.8 | 155.9 - 156.3 | 144.1 - 144.2 |
| 1.2 - 1.3 | 53-55 | 0.0161 - 0.0162 | 147.5 - 147.9 | 157.7 - 158.1 | 156.2 - 156.5 | 144.2 - 144.3 |

FIG. 8

| f1 [dB]       | f2 [dB]       | f3 [dB]       | f4 [dB]       |
| ------------- | ------------- | ------------- | ------------- |
| 0.5 [MHz]     | 1.2 [MHz]     | 2.5 [MHz]     | 5.0 [MHz]     |
| 146.7 - 147.2 | 156.9 - 157.4 | 155.6 - 156.0 | 143.9 - 144.1 |

FIG. 9

SUSPENDED SEDIMENT METER

The application relates to a system and a method for determining concentration of suspended sediment in a fluid.

Water monitoring techniques, which measure low and high suspended sediment concentrations (SSC) of water, can be used to optimize or improve processes for various industrial applications.

In one application, the water monitoring techniques are used for monitoring water quality, wherein the monitoring is located near construction sites where any increase of suspended sediment in the water may be a hazard for nature, such as corals, fishes, or sea grass. In another application, the water monitoring techniques are used for real-time control of suspended sediment in an intake and/or in an outlet of hydropower plants to prevent damage of parts of the hydropower plants, such as pumps, turbine shaft seals, valves, and gates. In a further application, these water monitoring techniques are used for controlling intake of sewage water for water treatment plants.

Different acoustic backscattering (ABS) technologies exist to measure concentration of suspended sediment for monitoring quality of water. These methodologies often require calibrations, wherein samples of the fluid are taken for analysing the suspended sediment of the fluid samples. The analysis includes converting backscatter intensity measurements, like echo levels (EL), to suspended sediment concentrations (SSC) data.

Such sampling needs to be done regularly to avoid providing the same measurement value for different compositions of the suspended sediment. The same measurement value can be obtained from different suspended sediment with certain particle sizes. Composition of the suspended sediment can vary in situations, such as natural fluctuations, wherein different soil run-offs into the water changes in industrial processes or changes in households that impact sewage water-discharge from the said households.

EP 0 989 397 A1 discloses a process for determining the characteristics of dispersed particles. The process involves directing acoustic or light waves into a dispersion of particles, and measuring attenuation of the waves for particular frequencies to provide an attenuation spectrum. The measured attenuation spectrum is then compared to a set of theory-based calculated attenuation spectra to determine the particle size distribution corresponding to the measured attenuation spectrum.

U.S. Pat. No. 4,706,509 discloses simultaneous measuring of concentration of solids and particle size distribution in a suspension, which is effected by exciting the suspension with ultrasonic waves of a plurality of frequencies. The wavelength of the lowest frequency is greater than the diameter of the largest particles to be expected and the wavelength of the highest frequency is smaller than the diameter of the smallest particles to be expected. The dimensional spectrum of the solid particles is divided into a plurality of dimensional intervals. The respective solids concentrations are determined by measuring the radiation absorption of each frequency used for irradiation and representing the same as the sum of the products of the absorption coefficients, which are specific of the frequency and dimensional interval with the unknown particle concentrations. This results in a linear system of equations, which is solved with respect to the unknown concentrations.

It is an object of the application to provide an improved method of measuring suspended sediment in fluid.

The application provides a device for measuring at least one parameter value of a suspended sediment of a fluid. This measuring device is called a sediment meter.

The fluid here refers to a liquid although it can also refer to a gas. The sediment has a plurality of particles with different sizes.

Some examples of the sediment parameter include a concentration of the sediment, a median size of a particle function of the sediment, and a slope of a particle function of the sediment, although other parameters of the sediment are also possible.

The term "median" here refers to a middle number in a set of numbers that have been arranged in order or to a measurement in a set of measurements that have been arranged in order. The term "median" also refers to a mean or an average amount or figure.

The device includes a backscattering transducer module, a storage unit, and a calculation unit.

The backscattering transducer module comprises a source module and a receiver module.

The source module is provided for transmitting at least three acoustic signals with different fixed characterising measurement frequencies and with pre-determined signal levels.

Different from attenuation measurements where an acoustic signal or a light wave is directed into dispersion and measuring the attenuation of the wave, the acoustic signals of this application are intended for directing at the suspended sediment that is of interest to the user and for being echoed back. The acoustic signals experience energy or attenuation as they travel in the fluid to the sediment. The sediment then scatters the acoustic signals and also backscatters the acoustic signals towards the transducer module, whereby the acoustic signals are further attenuated. The backscattered acoustic signals are also called echo signals.

The receiver module measures at least three echo level values of the at least three echo signals, which correspond with the at least three acoustic signals.

Generally, the number of sediment parameters for describing or characterising the sediment is three. These three sediment parameters also represent three unknowns. Hence, the number of acoustic signals for obtaining information about the sediment is also three.

In reality, one or more of the acoustic signals may not obtain information about the sediment. The acoustic signal may have a frequency that does not generate a backscattering signal from the sediment. Hence, more than three acoustic signals can be used to characterise the sediment.

The storage unit stores a data set of pre-determined echo level values with a corresponding data set of pre-determined suspended sediment parameter values for different operating frequencies of the sediment meter. In other words, the storage unit has various pre-determined echo level values for the different operating frequencies of the sediment meter. Each pre-determined echo level value has corresponding pre-determined suspended sediment parameter values.

The calculation unit derives one or more suspended sediment parameter value according to the stored data sets of the storage unit and according to the measured echo level values from the receiver module. The calculation unit compares the measured echo level values with the stored data set of pre-determined echo level values with the stored corresponding data set of pre-determined suspended sediment parameter values to derive the sediment parameter values.

The measuring device has an advantage of a simple design for producing accurate sediment readings.

The data set of pre-determined suspended sediment parameter values often includes at least one concentration suspended sediment parameter value, and/or at least one median parameter value of a particle function of the suspended sediment, and/or at least one slope parameter value of the particle function of the suspended sediment. These sediment parameters are often used to describe the sediment.

The calculation unit often includes a module for detecting a presence of air bubbles, which are placed in the signal path of the acoustic signals, by deriving at least one parameter value of the echo signal.

The user can be presented with a warning message if the presence of air bubbles is detected.

The parameter value of the echo signal can comprise a phase parameter value of the frequency spectrum of the echo signal. The phase parameter value can be derived using Fast Fourier Transform techniques. The phase parameter values for only sediment usually lies in a typical pre-determined range. When the phase parameter values are outside this range, this indicates that the phase parameter values have shifted and this shift can be caused by air bubbles in the fluid.

The parameter value of the spectrum of the echo signal can also comprise an amplitude parameter value of the frequency spectrum of the echo signal. This amplitude parameter value can also be derived using Fast Fourier Transform techniques. A main amplitude parameter value usually occurs at an operating frequency of the acoustic signals. When a significant-amplitude occurs at a higher harmonic or lower sub-harmonic frequency, this also indicates a presence of air bubbles. An amplitude at the higher harmonic frequency would be caused by the oscillation effect of the air bubbles while an amplitude at the sub-harmonic frequency would be generated by non-linear interactions between the acoustic wave and the air bubbles. The significant amplitude is defined as amplitude that is bigger than a pre-determined threshold value.

The application also provides a method of determining at least one parameter of a suspended sediment of a fluid.

The method includes a step of providing a data set of pre-determined echo level values with a corresponding data set of pre-determined suspended sediment parameter values. A main computer can be used to generate these data sets.

After this, at least three acoustic signals with different fixed characterising measurement frequencies are directed at the suspended sediment of the fluid, which is of interest to the user.

The acoustic signals travel in the fluid to the sediment where the sediment scatters and reflects back the acoustic signals. The reflected acoustic signals are called echo signals.

At least three echo levels of at least three echo signals, which correspond with the at least three acoustic signals, are then measured.

At least one parameter value of the suspended sediment are later derived according to the provided data set of pre-determined echo level values with the provided corresponding data set of pre-determined suspended sediment parameter values and according to the measurements of the at least three echo levels.

The data set of pre-determined suspended sediment parameter values often comprises a pre-determined concentration suspended sediment parameter value, and/or a pre-determined median parameter value of a particle function of the suspended sediment, and/or a pre-determined slope parameter value of the particle function of the suspended sediment. These parameter values are easy to understand and are often used to describe the sediment.

The method often includes a step of detecting a presence of air bubbles in the signal path of the acoustic signals. The air bubbles can affect the readings of the sediment of interest to the user.

The user can be presented with a warning message if the presence of air bubbles is detected.

The detection of the presence of air bubbles usually includes a step of deriving at least one phase parameter value of the frequency spectrum of the echo signal. The phase parameter value of the echo signal usually falls within a pre-determined range. When the phase parameter value lies outside this range, the phase parameter value has shifted and this can be caused by air bubbles that are placed in the measurement path of the sediment meter.

The detecting of the presence of air bubbles can also include a step of deriving at least one amplitude value of the frequency spectrum of the echo signal. A main amplitude often occurs at the operating frequency of the acoustic signals. When a significant amplitude occurs at for example higher harmonic frequency, this indicates the presence of air bubbles. The significant amplitude is bigger than a pre-determined threshold value.

The three echo levels can also be converted from the measured electrical signal for easy computation of the sediment parameter values.

The deriving of the at least one suspended sediment parameter often takes in account effects of attenuation due to the fluid, and/or effects of attenuation due to particle sizes of the suspended sediment, and/or effects of concentration of the suspended sediment. These are done for a more accurate measurement of the sediment.

Figure 2:
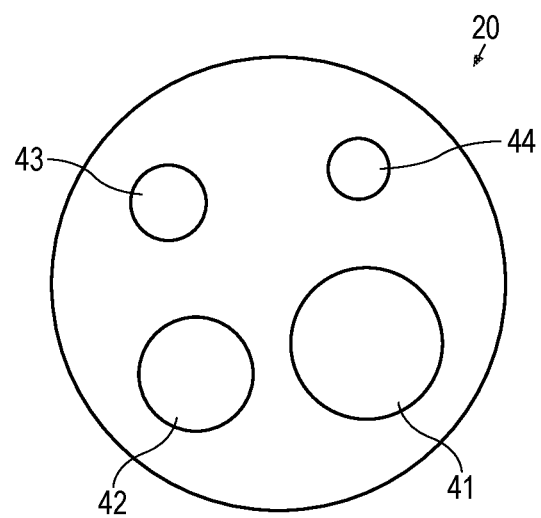
Figure 3:
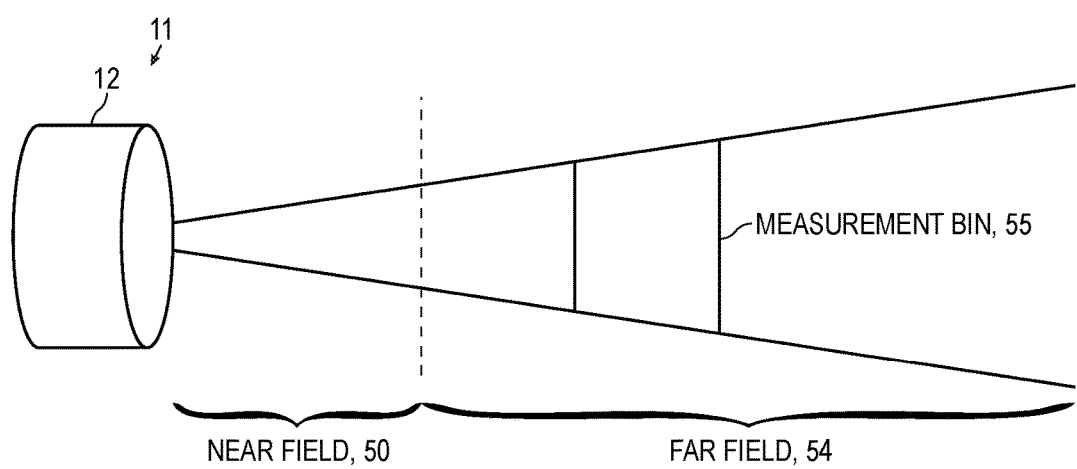
Figure 4:
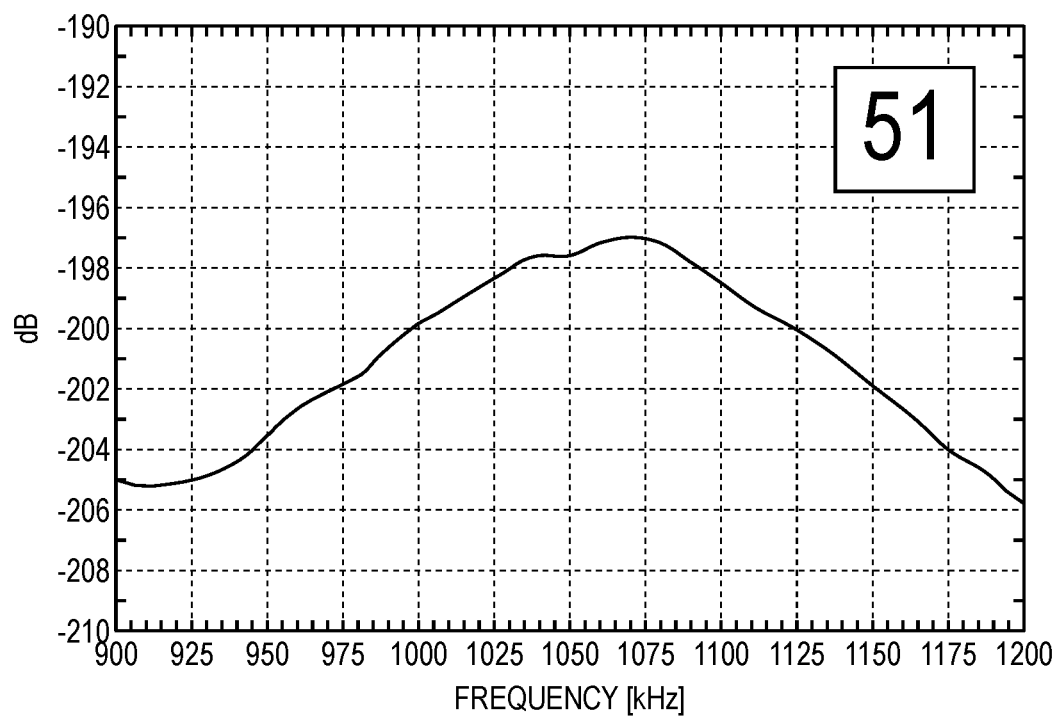
Figure 5:
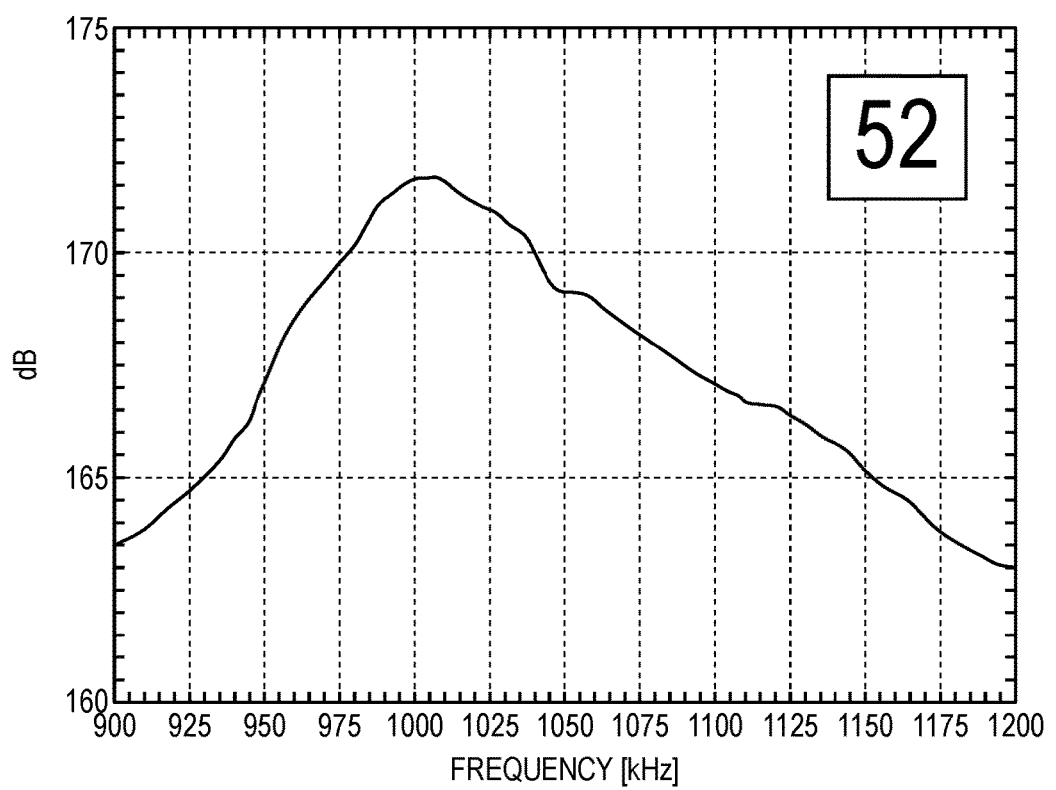
Figure 6:
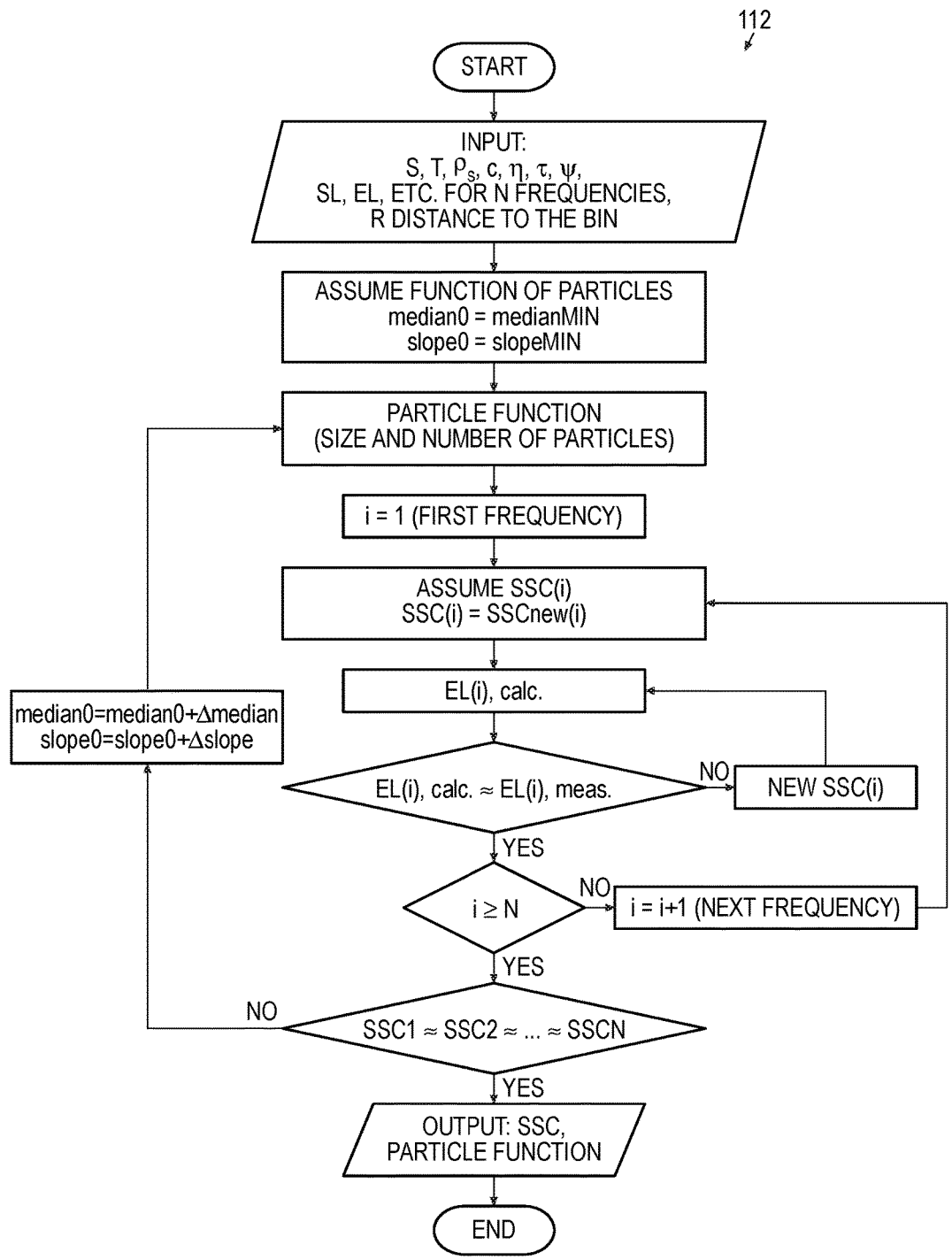
Figure 7:
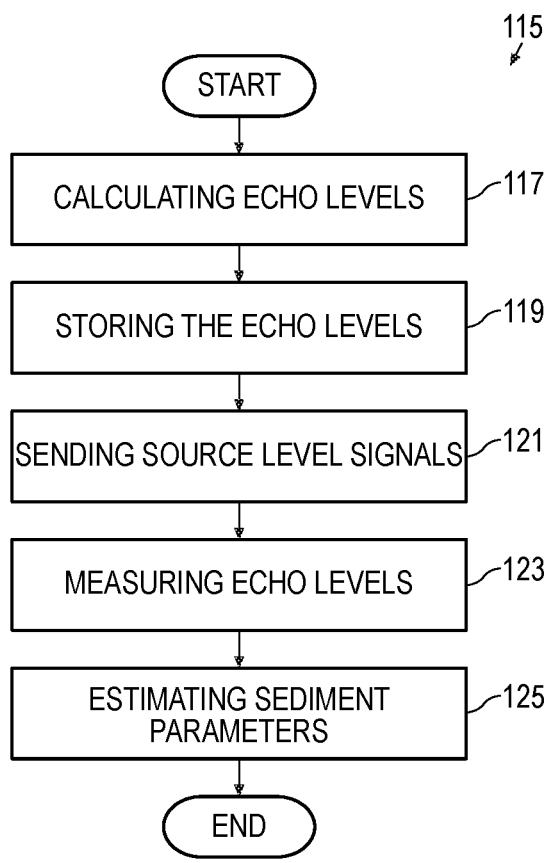
Figure 10:
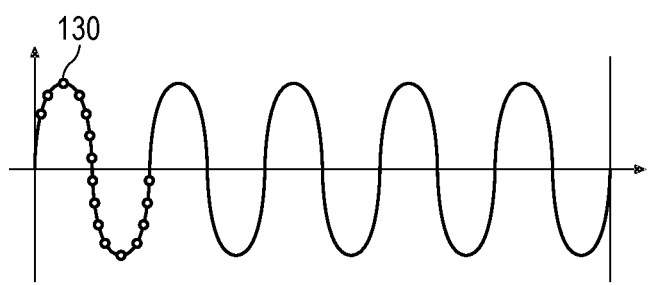
Figure 11:
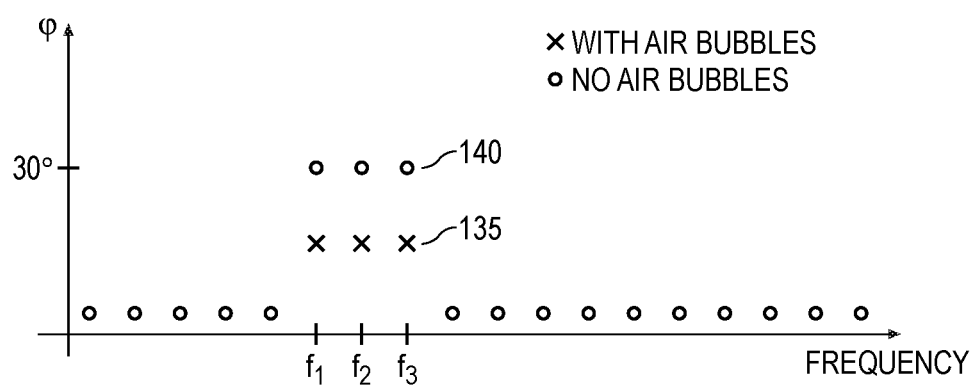
Figure 12:
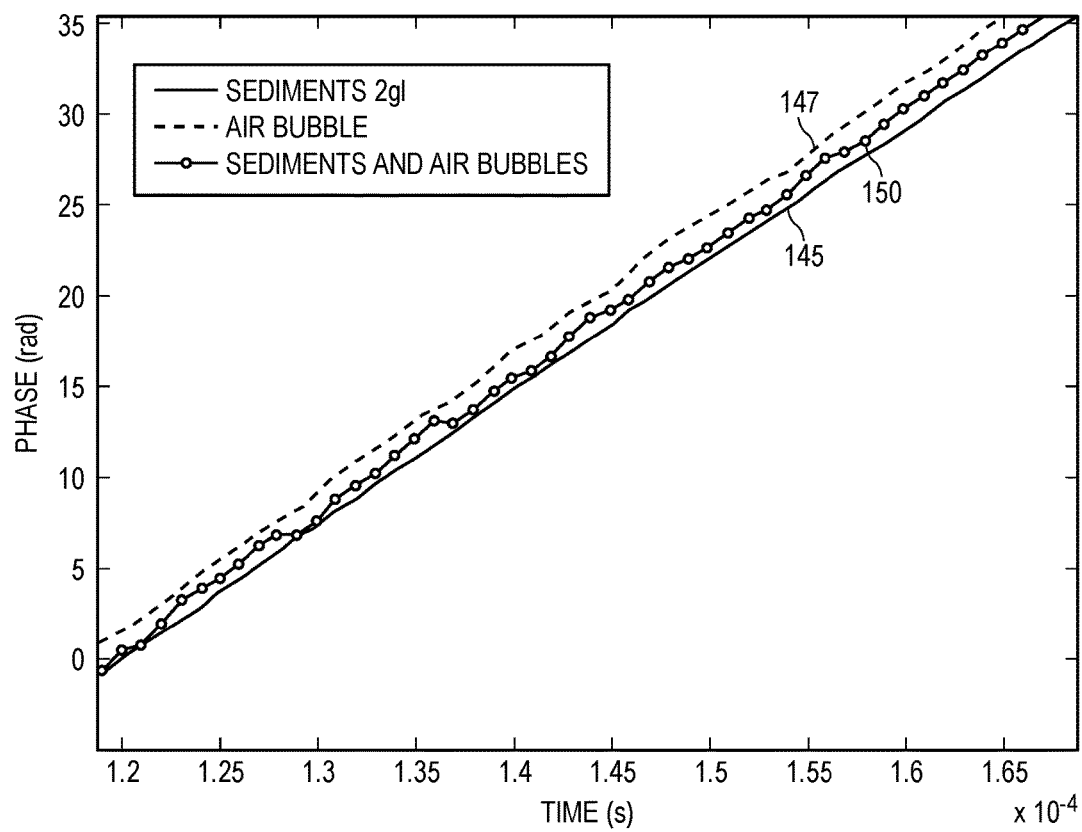
Figure 13:
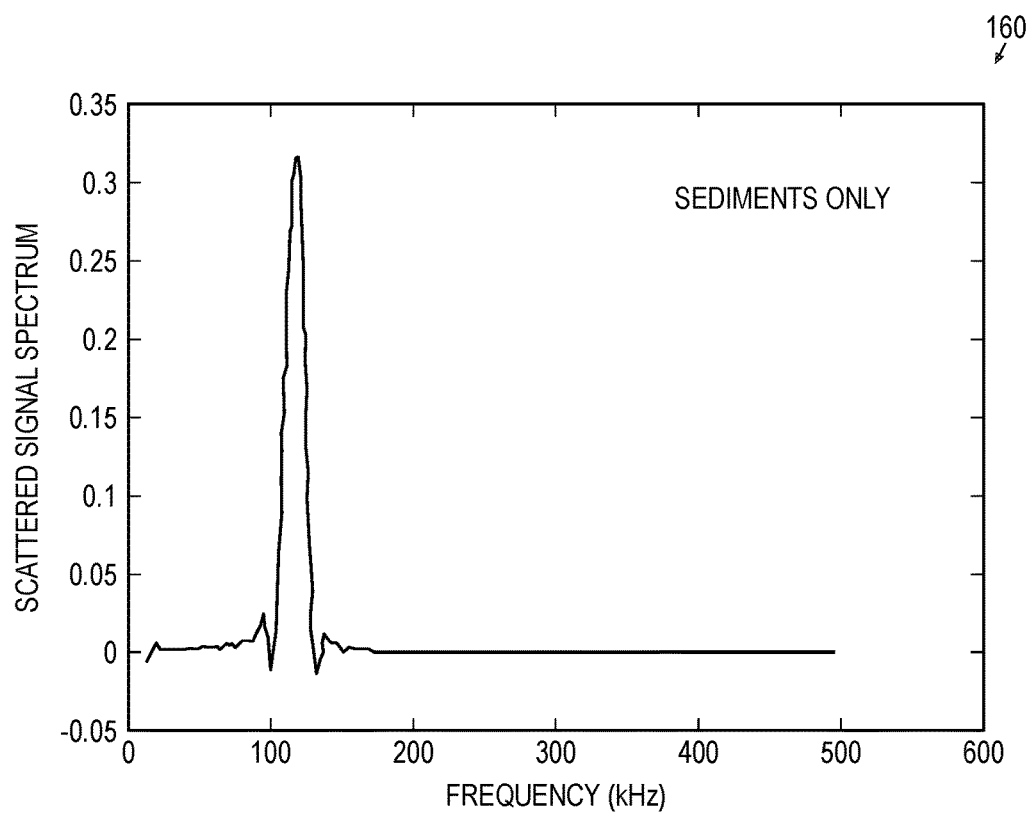
Figure 14:
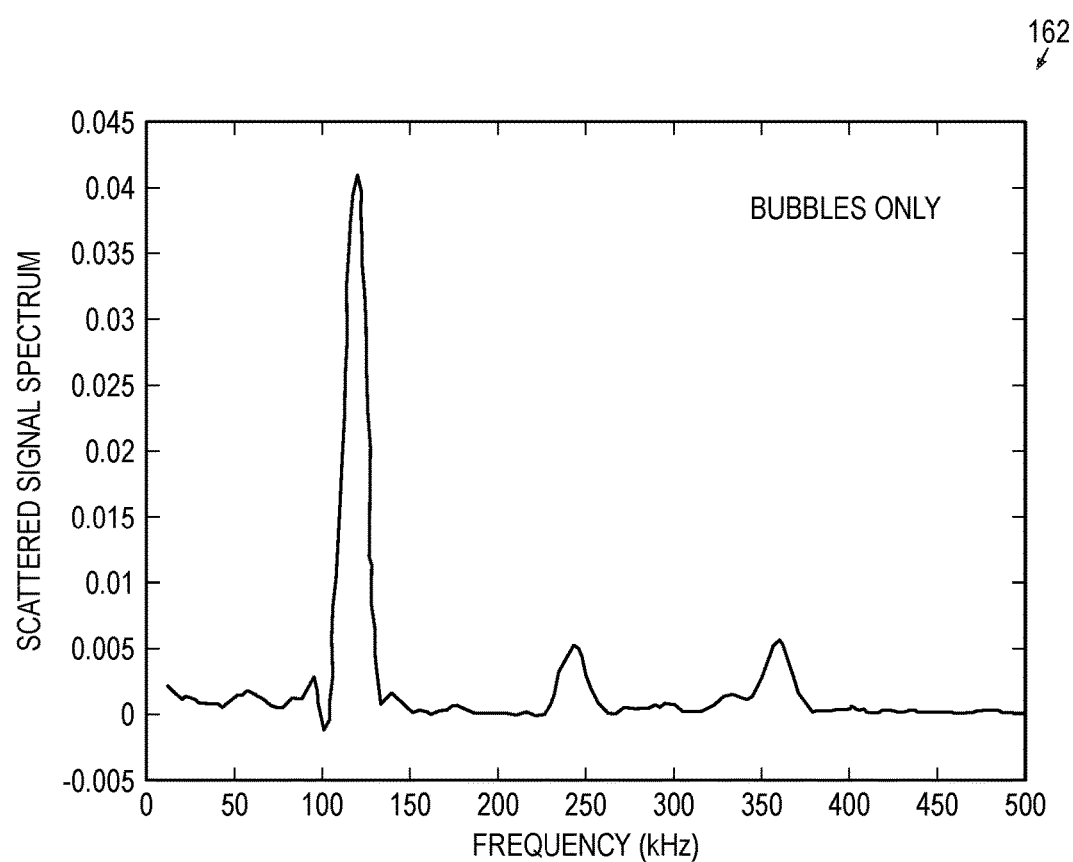
Figure 15:
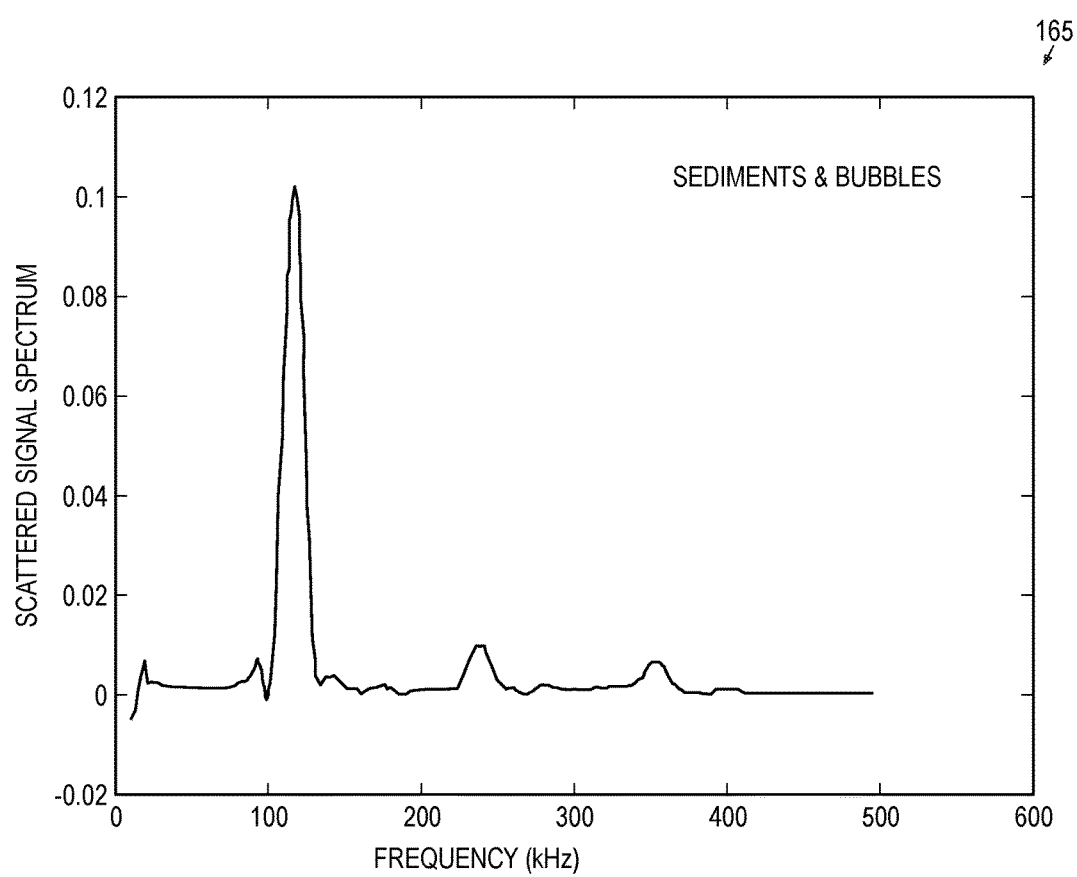

FIG. 1 illustrates a suspended sediment meter,

FIG. 2 illustrates a transducer head of the suspended sediment meter of FIG. 1, the transducer head includes a plurality of transducers, FIG. 3 illustrates an operating field of the transducer head of FIG. 2, FIG. 4 illustrates a receiving sensitivity graph of one of the transducers of the transducer head of FIG. 2, FIG. 5 illustrates a transmitting sensitivity graph of one of the transducers of the transducer head of FIG. 2, FIG. 6 illustrates a flow chart of a method for measuring suspended sediment concentration (SSC), FIG. 7 illustrates a flow chart of a method of using the sediment meter of FIG. 1 to determine suspended sediment parameters, FIG. 8 illustrates a table of stored values of the sediment meter of FIG. 1 of the method of FIG. 7, FIG. 9 illustrates ranges of measurement values of the method of FIG. 7, FIG. 10 illustrates measurement points of backscattered signals of suspended sediment of a method for detecting air bubbles, FIG. 11 illustrates a view of phases of the backscattered signal of FIG. 10, FIG. 12 illustrates another view of phases of the backscattered signal of FIG. 10, FIG. 13 illustrates a signal spectrum of a backscattered signal of the suspended sediment meter of FIG. 1 of another method of detecting presence of air bubbles, FIG. 14 illustrates a further signal spectrum of a backscattered signal BS of the suspended sediment meter of FIG. 1 for detecting presence of air bubbles, and FIG. 15 illustrates another signal spectrum of a backscattered signal BS of the suspended sediment meter of FIG. 1 for detecting presence of air bubbles.

In the following description, details are provided to describe embodiments of the application. It shall be apparent to one skilled in the art, however, that the embodiments may be practiced without such details.

Some parts of the embodiments, which are shown in the Figs., have similar parts. The similar parts have the same names or similar part numbers with a prime symbol or with an alphabetic symbol. The description of such similar parts also applies by reference to other similar parts, where appropriate, thereby reducing repetition of text without limiting the disclosure.

FIG. 1 shows a suspended sediment meter 10. The sediment meter 10 comprises a processor 15, a memory unit 17, and a transducer head 20. The processor 15 is connected to the memory unit 17 and to the transducer head 20. The sediment meter 10 also includes an air bubble detector 18.

As seen in FIG. 2, the transducer head 20 includes a transducer 41, a transducer 42, a transducer 43, and a transducer 44. Each of the transducers 41, 42, 43, and 44 has an acoustic source and an acoustic receiver.

In use, the suspended sediment meter 10 is used for determining one or more parameters or characteristics of a suspended sediment of a fluid. An example of the parameter is a concentration of the suspended sediment. The suspended sediment is also called suspended material. The fluid here refers to a liquid, such as water.

For operational efficiency, the transducers 41, 42, 43, and 44 are often in physical contact with the fluid. A user directs the transducers 41, 42, 43, and 44 towards an area or a volume of the fluid that contains the suspended sediment, wherein the fluid area is of interest to the user.

The acoustic sources of the transducers 41, 42, 43, and 44 are intended for transmitting short pulses of source acoustic signals with various different frequencies to the fluid area, which is of interest to the user.

Pulse widths and frequencies of the transmitted pulses of the source acoustic signals are selected according to expected particle sizes of the suspended sediment, which are expected to be present in the fluid area. The source acoustic pulses then interact with the said suspended sediment, wherein the suspended sediment scatters the source acoustic pulses and reflects the source acoustic pulses back to the acoustic receivers of the transducers 41, 42, 43, and 44. In other words, the suspended sediment backscatters the source acoustic pulses to the said acoustic receivers. The reflected acoustic pulses are also called echo signals, raw signals, or backscattered signals.

In one example, the transducer 41 produces an acoustic signal with an operating frequency of 0.5 MHz (megahertz) while the transducer 42 produces an acoustic signal with an operating frequency of 1 MHz. The transducer 43 produces an acoustic signal with an operating frequency of 2 MHz and the transducer 44 produces an acoustic signal with an operating frequency of 4 MHz.

In another example, the source acoustic pulses have a transmission range of about several meters, a pulse width of about 10 microseconds, and a frequency ranging from about 0.250 MHz (megahertz) to about 5 MHz for measuring particle sizes with diameter ranging from about 2 mm (millimeter) to about 20 μm (micrometer).

The air bubble detector 18 acts to detect presence of air bubbles in the fluid, which can affect readings of suspended sediment.

FIG. 3 shows an operating area or field of acoustic signals of a sonar transducer 11 that corresponds to the transducers 41, 42, 43, and 44 of the transducer head 20 of the suspended sediment meter 10.

The operating area can be roughly divided into two regions, namely a near field 50 and a far field 54. The near field 50 is placed between the transducer 11 and the far field 54. The far field 54 includes a measurement bin 55.

The measurement bin 55 refers to a volume that contains a portion of a suspended sediment of a fluid, which is of interest to the user. The length of the measurement bin, which is measured radially along a line that originates from the transducer 11 to the measurement bin, defines a number of cycles of a frequency of the acoustic signals that is required to extend throughout the measurement bin to ensure that the measurement bin contains the acoustic signals for backscattering the acoustic signals.

In one implementation, the suspended sediment is located at least 30 cm (centimeter) from the surface of the transducer 11. The length of the measurement bin 55 is 3 cm. In this example, for an acoustic signal with a frequency of 1 MHz, the number of pulses for extending throughout the measurement bin is about 20 cycles whereas for an acoustic signal with a frequency of 4 MHz, the number of pulses for extending throughout the measurement bin is about 80 cycles.

The transducer 11 acts as a source of acoustic signals that are directed at the said sediment portion. The shape and the dimensions of the transducer 11 have an impact on spatial resolution of the suspended sediment and also an impact on characteristics of backscattered signals, which are associated with the acoustic signals.

The acoustic signals in the near field 50 are usually more complex to analysis than the acoustic signals in the far field 54. In the far field 54, the acoustic signals of the acoustic source can be treated and be considered as originating from a point source. If the transducer 11 has a circular shape, the interacting volume of its acoustic signal in the far field 54 may be approximated as having a cone shape with a tip of the cone shape being located at the transducer 11. On the other hand, in the near field 50, the acoustic signals of the acoustic source can be considered as be emitted in a narrow column to the near field 50.

In a general sense, the sonar transducer 11 can also produce specific, non-conical beam patterns. The measurement bin 55 can also be in located in the near field 50, instead of being located in the far field 54.

Referring to the acoustic receivers of the transducers 41, 42, 43, and 44, they measure intensities of echo signals, which are associated with the source acoustic signals of the acoustic sources of the transducers 41, 42, 43, and 44. The intensity data comprises magnitude data and phase shift data. The magnitude data is also called strength data.

The acoustic receiver measures backscattered signals BaS of the source acoustic signals in millivolts (mV). The millivolt value is then converted to dB (decibel) values by applying specific transducer sensitivity SE for the relevant frequency using an equation that is shown below.

$$EL[db] = 20 \log_{10}(BaS) + SE \qquad (2),$$

wherein
EL=(received) echo level,
BaS=measured backscattered signals
SE=transducer sensitivity The value of the transducer sensitivity SE is shown in a receiving sensitivity graph 51, which is illustrated in FIG. 4. The transducer sensitivity SE is also called transducer responsivity. The transducer responsivity is defined as gain of output signal with reference to input signal.

The echo level EL is also known as an intensity of the backscattered signals.

In a similar manner, the decibel values of the source level SL are calculated using a transmitting sensitivity graph 52, which is illustrated in FIG. 5, for a signal that is produced by a transducer with a 1 MHz frequency.

The measured intensity of the echo signals can be described using a mathematical equation, called a "Sound Navigation And Ranging" (SONAR) equation, which is shown below.

$$EL = SL - TL + BS \quad (1),$$

wherein
- EL=(received) echo level,
- SL=source level,
- TL=transmission loss, and
- BS=backscatter strength.

Taking into account speed of sound in the fluid, sound propagation characteristics, and scattering strength of the suspended sediment, a relationship between the source level SL signals and characteristics of the suspended sediment can be developed. This relationship is dependent on the frequencies of the source level SL signals.

An echo level EL of a backscattered signal from a uniform field of suspended sediment particles in a fluid with constant concentration is considered to vary inversely with a distance between an acoustic source of a source level SL signal and particles of the suspended sediment and to vary according to correlation factors for attenuation due to the fluid and to the suspended sediment particles.

The echo level EL of the backscattered signal can thus be correlated with a concentration and particle size of the suspended sediment and with time delay between transmitting of the acoustic signal and receiving of the backscattered signal of acoustic signal.

A mathematical relationship model for the above described relationship is shown below.

$$EL = SL + C - 20\log(\eta R) - 2\alpha_w R - 2\left[\sum\left(C_1 \frac{\chi_i SSC_i}{a_i \rho_s}\right)\right] R + 10\log\left(\psi \frac{c\tau}{2}\right) + 10\log\sum(C_2 a_i^2 f_{\#,i}^2 N_i) \quad (3)$$

wherein
- EL=(received) echo level,
- SL=source level,
- C=coefficient that is dependent on the transducer,
- R=distance between an acoustic source and a measurement bin, the bin being defined as a range between two distances R1 and R2, wherein the selection of the two distances R1 and R2 is done carefully to ensure that the measurement bin contains the suspended sediment of interest for measuring the desired information, for example particle mixture,
- $\eta = f(R, a_r)$=near field correction,
- $\alpha_w = f(f_R, S, T, \text{etc})$=absorption due to the fluid, wherein $f_R$=frequency, S=salinity, and T=temperature,
- $\psi$=solid opening angle of the transducer,
- $SSC_i$=Suspended Sediment Concentration of i-th fraction,
- $c = f(f_R, S, T, \text{etc})$=sound speed,
- $\tau$=duration of the transmitted signals,
- $N_i$=number of particle per unit volume,
- $a_i$=particle radius,
- $\chi_i$=normalized total scattering cross-section,
- $f_{\#,i}$=form function,
- $\rho_s$=density of sediments,
- $C_1$=function of sediment concentration, and
- $C_2$=function of sediment concentration.

The equation (3) takes into consideration transmission loss or attenuation of signal due to spreading, to fluid and to the suspended sediment.

In particular, the term $20 \log(\eta R)$ represents a component of the transmission loss TL that is due to spreading. The term $2\alpha_w R$ represents another component of the transmission loss TL that is due to the fluid. The term $$2\left[\sum\left(C_1 \frac{\chi_i SSC_i}{a_i \rho_s}\right)\right] R$$

represents a further component of the transmission loss TL that is due to the suspended sediments.

The terms $$10\log\left(\psi \frac{c\tau}{2}\right) + 10\log\sum(C_2 a_i^2 f_{\#,i}^2 N_i)$$

represent the backscatter strength BS of the source level SL signals.

The coefficients or parameters $C_1$ and $C_2$ are also defined as functions of the sediment concentration, instead of constant values of the sediment concentration, for improving accuracy of determining the echo levels EL over a wider range of the suspended sediment concentration (SSC) values.

Referring to the memory unit 17, it serves to store a table of the determined echo levels EL with corresponding sediment parameters.

The processor 15 acts to determine parameters of the suspended sediment according to the determined echo levels EL.

Referring to the suspended sediment, the suspended sediment can be described with three sediment parameters, namely the suspended sediment concentration parameter together with the median parameter and with the slope parameter of the particle function of the suspended sediment. This is explained below.

Different methods for determining the suspended sediment parameters are possible.

FIG. 6 shows a flow chart 112 of a method of metering for measuring suspended sediment concentration (SSC) using multi-frequency acoustic backscattering (ABS).

The flow chart 112 includes a step of transmitting three different signals of acoustic pulse to the suspended sediment of the fluid of interest, wherein the three signals have three corresponding frequencies. After this, backscattered signals, which are associated with the three different signals, are measured.

FIG. 7 shows a flow chart 115 of a method of using the sediment meter 10 to determine the suspended sediment parameters is described below.

The method includes a preparation step and an operating step.

The preparation step comprises calculation of a plurality echo level EL values for pre-determined source level SL signals using the equation (3) for various pre-determined values of the suspended sediment parameters, in a step 117.

These values are then stored in the memory unit 15 of the sediment meter 10, in a step 119.

FIG. 8 shows a table 120 of stored data set of sediment parameters.

The table 120 comprises several columns of data. The data includes
- a column of data of ranges of SSC values of a suspended sediment,
- a corresponding column of data of ranges of median values of particle function of the sediment,
- a corresponding column of data of ranges of slope values of the particle function of the sediment,
- a corresponding column of data of ranges of echo levels for a source signal with a frequency of 0.5 Mhz,
- a corresponding column of data of ranges of echo levels for a source signal with a frequency of 1.2 Mhz,
- a corresponding column of data of ranges of echo levels for a source signal with a frequency of 2.5 Mhz, and
- a corresponding column of data of ranges of echo levels for a source signal with a frequency of 5.0 Mhz.

Referring to the operating step, it comprises sending three source level SL signals with three different corresponding frequencies of the sediment meter 10 to the suspended sediment, in step 121.

The sediment meter 10 later measures three echo level EL values that are associated with the three source level SL signals, in a step 123.

FIG. 9 shows a table 124 of ranges of the measured echo level EL values.
4

Using the stored values in the memory unit 15, three parameters of the suspended sediment are then estimated, in a step 125.

The three sediment parameters represent three unknown factors. The three source level SL signals with three different corresponding frequencies are then sufficient to obtain the values of the three sediment parameters.

For measured echo levels with readings between the range of 146.7 to 147.2 (dB) for a source signal with a frequency of 0.5 Mhz, the Suspended Sediment Concentration (SSC) parameter of the suspended sediment is then estimated as between 1.0 and 1.1 (kg/m3) with a median size parameter of particle function of the sediment estimated as between 53 and 55 μm (micrometer) and a slope parameter of the particle function of the sediment estimated as between 0.0161 and 0.0162, in a step 125.

The user often transmits more than three different signals with corresponding different frequencies, which can be four or five different frequencies, to ensure that the desired information is obtained from these signals. One of the frequencies of the acoustic signals may not generate backscattering signals when the said frequency does not generate backscattering signals for a particular particle size of the sediment. When this occurs, measurements of the backscattering signals will not contain any desired information.

The above method for determining suspended sediment parameters can also include steps for detecting air bubbles in the suspended sediment. The presence of air bubbles can adversely change the measured or determined sediment parameter values.

FIGS. 10 and 11 illustrate the evaluation of phases of backscattered signals of a suspended sediment of a method of detecting air bubbles, in a measurement bin of the fluid.

The method includes a step of taking discrete measurements 130 of the backscattered signals, as shown in FIG. 10.

The processor 15 then provides a Fourier transformation, such as Fast Fourier Transform (FFT), of the discrete measurements 130 in order to evaluate its phase spectrum. The phase values of the measurement frequencies in the phase spectrum have typical pre-determined range of values for fluids without air bubbles. Deviations from these phase values indicate the presence of air bubbles.

FIG. 11 shows different phases of the backscattered signals of the suspended sediment, namely phases 140 of suspended sediment with no air bubbles and shifted phases 135 of suspended sediment with air bubbles.

FIG. 12 shows another view of phases of the backscattered signal of the suspended sediment. FIG. 12 shows a solid line 145 of typical phases of backscattered signals from only suspended sediments, a dotted line 147 of shifted phases of backscattered signals from only air bubbles, and a dotted connected line 150 of shifted phases of backscattered signals from both suspended sediments and air bubbles.

When the presence of air bubbles is detected, the user is warned or alerted about this.

This allows the user to take appropriate actions when the air bubbles are detected. The air bubbles can adversely affect the determined suspended sediment parameter values.

FIGS. 13 to 15 show different signal amplitude spectrums derived by calculating the Fourier Transform of the backscattered signals of a suspended sediment of another method of detecting the presence of air bubbles.

The amplitude spectrums are then analyzed to identify occurrence of significant amplitude values at higher harmonic frequencies in the amplitude spectrum, wherein the said occurrence indicates presence of air bubbles in the fluid. The significant amplitude values are bigger than a pre-determined threshold value, which is stored in the memory unit 15 of the sediment meter 10.

FIG. 13 shows a signal amplitude spectrum 160 of the backscattered signal of the suspended sediment. The signal is backscattered from only suspended sediments of a fluid. The backscattered signal is associated with an acoustic source signal AS with an operating frequency of 120 kHz. The amplitude spectrum 160 shows one main frequency of 120 kHz with essentially no higher harmonic frequencies.

FIG. 14 shows a signal amplitude spectrum 162 of the backscattered signal. The signal is backscattered from only air bubbles of a fluid. The backscattered signal is associated with an acoustic signal AS with an operational frequency of 120 k kHz. The amplitude spectrum 162 shows a main frequency of 120 kHz and higher harmonic frequencies that includes a higher harmonic frequency of 240 kHz and a higher harmonic frequency of 360 kHz.

FIG. 15 shows a signal amplitude frequency spectrum 165 of a backscattered signal. The signal is backscattered from suspended sediments and from air bubbles of a fluid. The backscattered signal is associated with an acoustic signal AS with an operating frequency of 120 kHz. The amplitude spectrum 165 shows a main frequency of 120 kHz and higher harmonic frequencies that includes a higher harmonic frequency of 240 kHz and a higher harmonic frequency of 360 kHz.

This detection of air bubbles is then used to warn the user that the measured sediment concentration can be incorrect due to the presence of air bubbles.

This step allows the user to take appropriate steps regarding the air bubbles. The air bubbles can adversely affect the determined suspended sediment parameter values.

In a general sense, the step of detecting the air bubbles can be done in parallel or at the same time as the step of determining the concentration of the suspended sediment. The step of detecting the air bubbles can be also done before or after the step of determining the concentration of the suspended sediment.

The embodiments can also be described with the following lists of features or elements being organized into items. The respective combinations of features, which are disclosed in the item list, are regarded as independent subject matter, respectively, that can also be combined with other features of the application.

1. A device for measuring at least one parameter value of a suspended sediment of a fluid, the device comprising
    a backscattering transducer module that comprises
        a source module for transmitting at least three acoustic signals with different fixed characterising measurement frequencies and
        a receiver module for measuring at least three echo level values of echo signals, which correspond with the at least three acoustic signals,
    a storage unit that stores a data set of pre-determined echo level values with a data set of pre-determined suspended sediment parameter values,
    a calculation unit for deriving at least one suspended sediment parameter value according to the data set of pre-determined echo level values with the data set of pre-determined suspended sediment parameter values and according to the at least three echo level values
2. The device according to item 1, wherein
    the data set of pre-determined suspended sediment parameter values comprises at least one concentration suspended sediment parameter value.
3. The device according to item 1 or 2, wherein
    the data set of pre-determined suspended sediment parameter values comprises at least one median parameter value of a particle function of the suspended sediment.
4. The device according to one of the above-mentioned items, wherein the data set of pre-determined suspended sediment parameter values comprises at least one slope parameter value of the particle function of the suspended sediment.
5. The device according to one of the above-mentioned items, wherein
    the calculation unit comprises a module for detecting a presence of air bubbles in the signal path of the acoustic signals by deriving at least one parameter value of the echo signal.
6. The device according to item 5, wherein
    the parameter value of the echo signal comprises a phase parameter value of the echo signal.
7. The device according to item 5, wherein
    the parameter value of the echo signal comprises an amplitude parameter value of the spectrum of the echo signal.
8. A method of determining at least one parameter of a suspended sediment of a fluid, the method comprising
    providing a data set of pre-determined echo level values with a data set of pre-determined suspended sediment parameter values,
    directing at least three acoustic signals with different fixed characterising measurement frequencies at the suspended sediment of the fluid,
    measuring at least three echo levels of echo signals, which correspond with the at least three acoustic signals,
    deriving at least one parameter value of the suspended sediment according to the data set of pre-determined echo level values with the data set of pre-determined suspended sediment parameter values and according to the measurements of the at least three echo levels.
9. The method according to item 8, wherein
    the data set of pre-determined suspended sediment parameter values comprises a pre-determined concentration suspended sediment parameter value.
10. The method according to item 8 or 9, wherein
    the data set of pre-determined suspended sediment parameter values comprises a pre-determined median parameter value of a particle function of the suspended sediment.
11. The method according to one of items 8 to 10, wherein
    the data set of pre-determined suspended sediment parameter values comprises a pre-determined slope parameter value of the particle function of the suspended sediment.
12. The method according to one of items 8 to 11 further comprising
    detecting a presence of air bubbles in the signal path of the acoustic signals.
13. The method according to item 12, wherein
    the detecting of the presence of air bubbles comprises deriving at least one phase parameter value of the echo signal.
14. The method according to item 12, wherein
    the detecting of the presence of air bubbles comprises deriving at least one amplitude value of the spectrum of the echo signal.
15. The method according to one of items 8 to 14, wherein
    the deriving of the at least one suspended sediment parameter takes in account effects of attenuation due to the fluid.
16. The method according to one of one of items 8 to 15, wherein
    the deriving of the at least one suspended sediment parameter takes in account effects of attenuation due to particle sizes of the suspended sediment.
17. The method according to one of the items 8 to 16, wherein
    the deriving of the at least one suspended sediment parameter takes in account effects of concentration of the suspended sediment.

Although the above description contains much specificity, this should not be construed as limiting the scope of the embodiments but merely providing illustration of the foreseeable embodiments. The above stated advantages of the embodiments should not be construed especially as limiting the scope of the embodiments but merely to explain possible achievements if the described embodiments are put into practice. Thus, the scope of the embodiments should be determined by the claims and their equivalents, rather than by the examples given.

REFERENCE NUMBERS 10 suspended sediment meter
11 sonar transducer
15 processor
17 memory unit
18 air bubble detector
20 transducer head
41 transducer
42 transducer
43 transducer
44 transducer
50 near field
51 receiving sensitivity graph
52 transmitting sensitivity graph
54 far field 55 measurement bin
112 flow chart
115 flow chart
117 step
119 step
120 table
121 step
123 step
124 table
125 step
130 discrete measurement
135 phase
140 phase
145 line
147 line
150 line
160 frequency spectrum
162 frequency spectrum
165 frequency spectrum

The invention claimed is:

1. A device for measuring at least one parameter value of a suspended sediment of a fluid, the device comprising
a backscattering transducer module that comprises
a source module for transmitting at least three acoustic signals with different fixed characterizing measurement frequencies and
a receiver module for measuring at least three echo level values of echo signals, which correspond with backscattered acoustic signals of the at least three acoustic signals with said different fixed characterizing measurement frequencies,
a storage unit that stores a data set of pre-determined echo level values with a data set of pre-determined suspended sediment parameter values,
a calculation unit for deriving at least one suspended sediment parameter value according to the data set of pre-determined echo level values with the data set of pre-determined suspended sediment parameter values and according to the at least three echo level values,
wherein the data set of pre-determined suspended sediment parameter values comprises at least one concentration suspended sediment parameter value.

2. The device according to claim 1, wherein the data set of pre-determined suspend sediment parameter values comprises at least one median parameter value of a particle function of the suspended sediment.

3. The device according to claim 1, wherein the data set of pre-determined suspended sediment parameter values comprises at toast one slope parameter value of the particle function of the suspended sediment.

4. The device according to claim 1,
wherein
the calculation unit comprises a module for detecting a presence of air bubbles in the signal path of the acoustic signals by deriving at least one parameter value of the echo signal.

5. The device according to claim 4, wherein
the parameter value of the echo signal comprises a phase parameter value of the echo signal.

6. The device according to claim 4, wherein
the parameter value of the echo signal comprises an amplitude parameter value of the spectrum of the echo signal.

7. A method of determining at least one parameter of a suspended sediment of a fluid, the method comprising
providing a data set of pre-determined echo level values with a data set of pre-determined suspended sediment parameter values,
directing at least three acoustic signals with different fixed characterizing measurement frequencies at the suspended sediment of the fluid,
measuring at least three echo levels of echo signals, which correspond with backscattered acoustic signals of the at least three acoustic signals with said different fixed characterizing measurement frequencies,
deriving at least one parameter value of the suspended sediment according to the data set of pre-determined echo level values with the data set of pre-determined suspended sediment parameter values and according to the measurements of the at least three echo levels,
wherein the data set of pre-determined suspended sediment parameter values comprises a pre-determined concentration suspended sediment parameter value.

8. The method according to claim 7, wherein
the data set of pre-determined suspended sediment parameter values comprises a pre-determined median parameter value of a particle function of the suspended sediment.

9. The method according to claim 7, wherein
the data set of pre-determined suspended sediment, parameter values comprises a pre-determined slope parameter value of the particle function of the suspended sediment.

10. The method according to claim 7 further comprising detecting a presence of air bubbles in the signal path of the acoustic signals.

11. The method according to claim 10, wherein
the detecting of the presence of air bubbles comprises deriving at least one phase parameter value of the echo signal.

12. The method according to claim 10, wherein
the detecting of the presence of air bubbles comprises deriving at least one amplitude value of the spectrum of the echo signal.

13. The method according to claim 7, wherein
the deriving of the at least one suspended sediment parameter takes in account effects of attenuation due to the fluid.

14. The method according to claim 7, wherein
the deriving of the at least one suspended sediment parameter takes in account effects of attenuation due to particle sizes of the suspended sediment.

15. The method according to claim 7, wherein
the deriving of the at least one suspended sediment parameter takes in account effects of concentration of the suspended sediment.

* * * * *